(12) United States Patent
Boyd et al.

(10) Patent No.: US 8,038,714 B2
(45) Date of Patent: *Oct. 18, 2011

(54) INTERVERTEBRAL SPACERS WITH SIDE WALL ACCESSIBLE INTERIOR CAVITY

(75) Inventors: Lawrence M. Boyd, Durham, NC (US); J. Kenneth Burkus, Columbus, GA (US); John D. Dorchak, Midland, GA (US); Bradley T. Estes, Durham, NC (US); Eddie F. Ray, III, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/383,191

(22) Filed: Mar. 20, 2009

(65) Prior Publication Data

US 2009/0254181 A1 Oct. 8, 2009

Related U.S. Application Data

(63) Continuation of application No. 09/869,813, filed as application No. PCT/US00/00604 on Jan. 11, 2000, now Pat. No. 7,534,265.

(60) Provisional application No. 60/115,388, filed on Jan. 11, 1999.

(51) Int. Cl.
*A61F 2/44* (2006.01)
(52) U.S. Cl. .................................................. 623/17.11
(58) Field of Classification Search ............... 623/17.11, 623/17.12, 17.16; 606/246, 279
See application file for complete search history.

(56) References Cited

U.S. PATENT DOCUMENTS

| | | |
|---|---|---|
| 2,519,811 A | 8/1950 | Alexander |
| 4,736,738 A | 4/1988 | Lipovsek et al. |
| 4,877,020 A | 10/1989 | Vich |
| 4,904,261 A | 2/1990 | Dove et al. |
| 4,950,296 A | 8/1990 | McIntyre |
| 5,423,825 A | 6/1995 | Levine |
| 5,593,409 A | 1/1997 | Michelson |
| 5,645,598 A | 7/1997 | Brosnahan, III |
| 5,658,337 A | 8/1997 | Kohrs et al. |
| 5,669,909 A | 9/1997 | Zdeblick et al. |
| 5,904,719 A | 5/1999 | Errico et al. |
| 6,033,438 A | 3/2000 | Bianchi et al. |
| 6,120,506 A | 9/2000 | Kohrs et al. |
| 6,165,219 A | 12/2000 | Kohrs et al. |
| 6,224,631 B1 | 5/2001 | Kohrs |
| 6,485,517 B1 | 11/2002 | Michelson |

FOREIGN PATENT DOCUMENTS

| | | |
|---|---|---|
| DE | 297 12 331 U1 | 11/1997 |
| EP | 0302719 | 2/1989 |
| EP | 0421485 | 4/1991 |
| FR | 2 724 312 A1 | 4/1995 |
| FR | 2 747 034 A1 | 4/1996 |
| FR | 2 762 779 A1 | 5/1997 |
| WO | WO 96/27348 | 9/1996 |
| WO | WO 96/39988 | 12/1996 |
| WO | WO 97/31517 | 8/1997 |
| WO | WO 98/17209 | 4/1998 |
| WO | WO 98/55052 | 12/1998 |

*Primary Examiner* — Eduardo C Robert
*Assistant Examiner* — David Comstock

(57) ABSTRACT

Intervertebral spacers and methods of promoting fusion bone growth in the space between adjacent vertebrae are provided. The spacers include an elongated body having a first end, a second end and an outer surface. Side walls connect the first and second ends. The elongated body also defines an interior cavity. The side wall defines an opening to the interior cavity in a side of the elongated body. At least one of the first and second ends has a discontinuity, such as a concave surface, for nesting with an adjacent spacer. The methods of promoting fusion bone growth include utilizing the inventive spacers described herein.

25 Claims, 13 Drawing Sheets

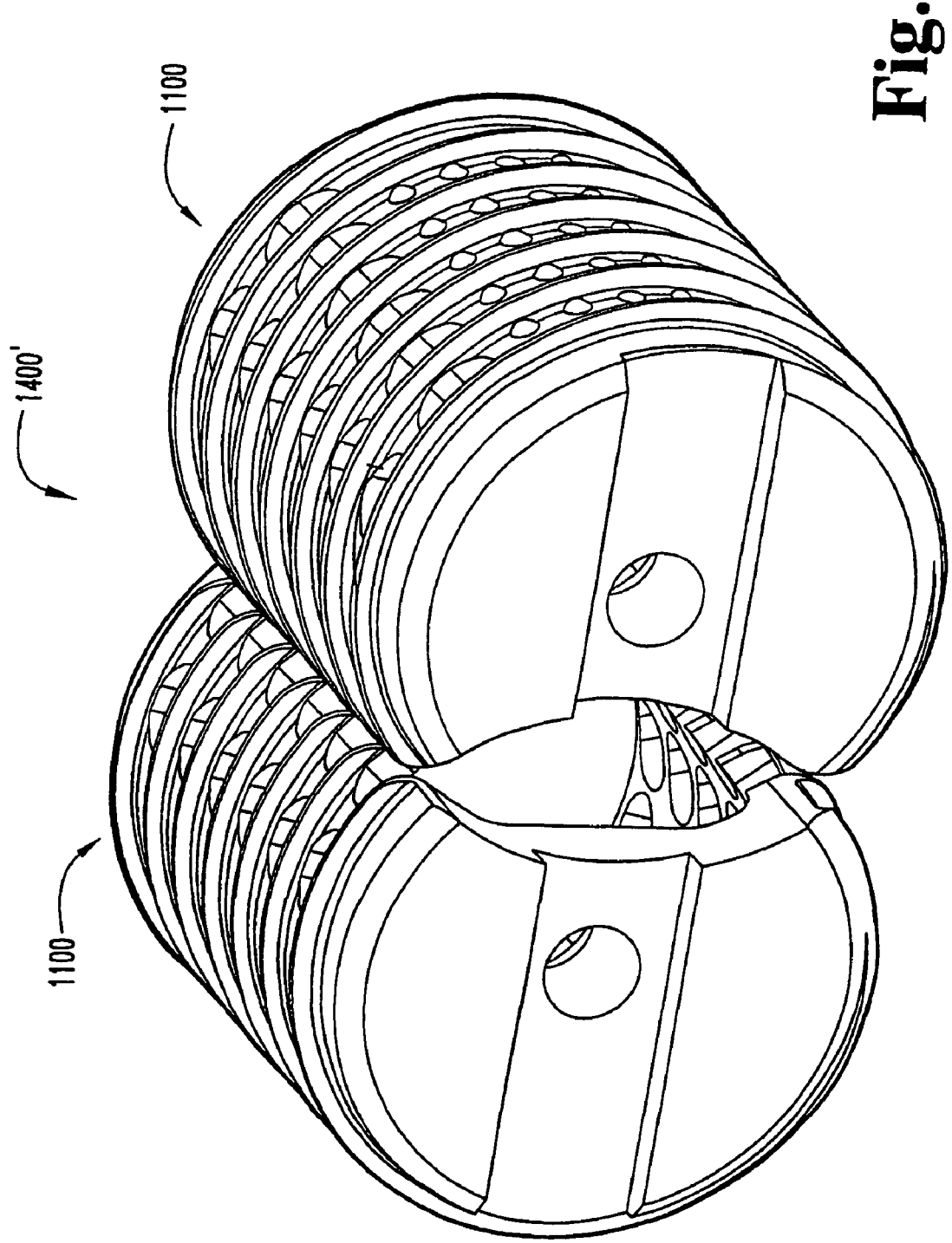

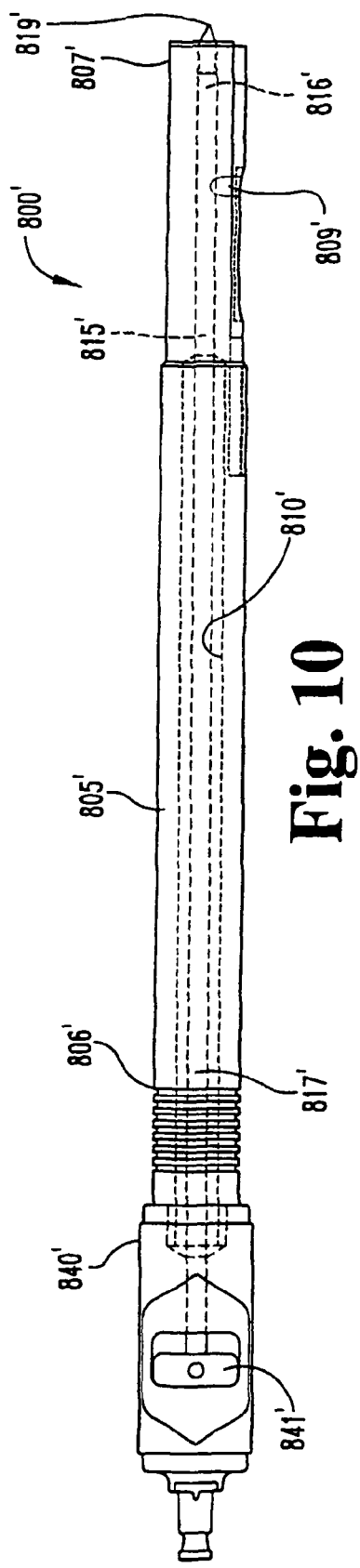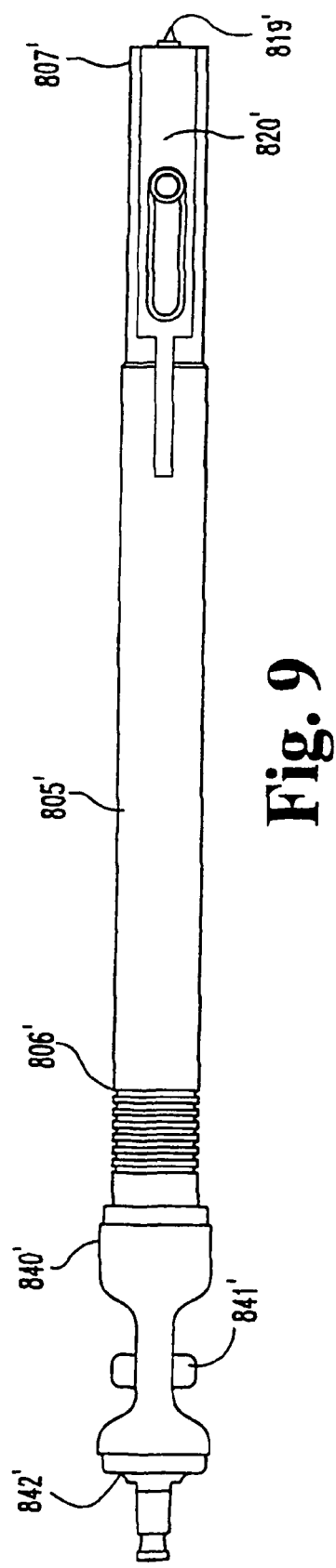
Fig. 10
Fig. 9

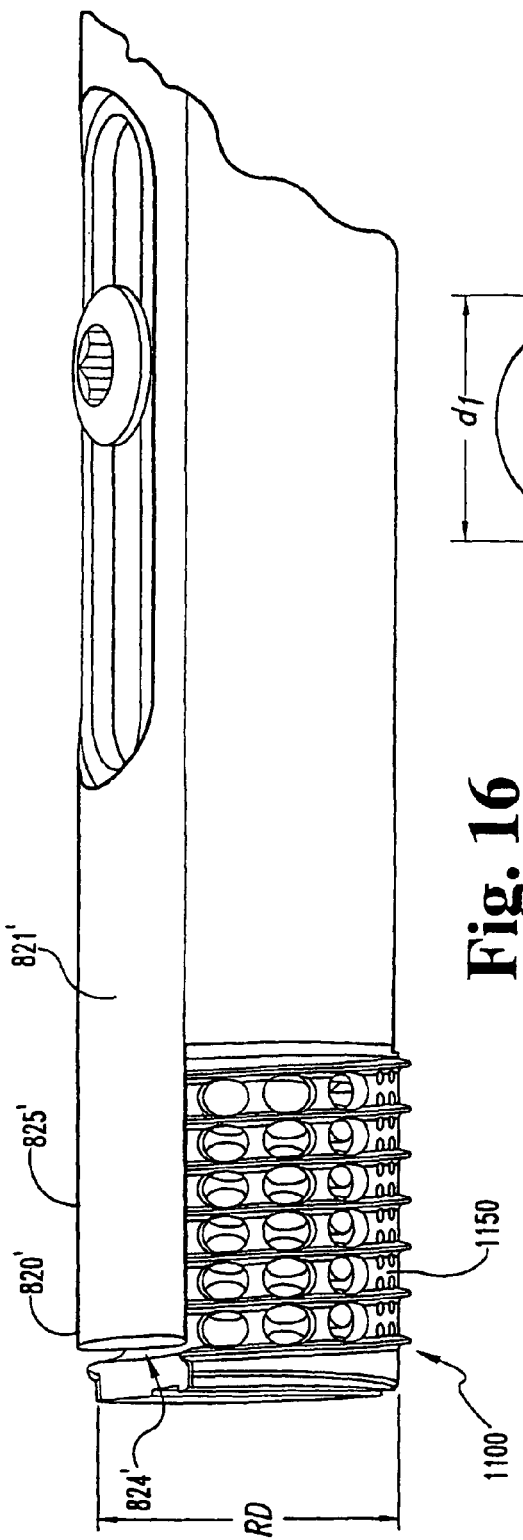
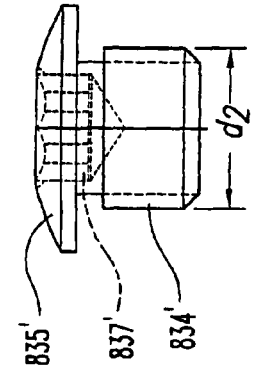
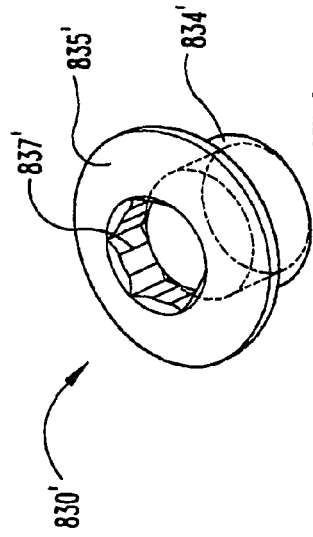

INTERVERTEBRAL SPACERS WITH SIDE WALL ACCESSIBLE INTERIOR CAVITY

The present application is a continuation of U.S. patent application Ser. No. 09/869,813, filed on Jan. 3, 2002, now U.S. Pat. No. 7,534,265, which is a national stage entry of International Application Number PCT/US00/00604 (WO 00/41655), filed on Jan. 11, 2000, which claims the benefit of U.S. Provisional Patent Application Ser. No. 60/115,388, filed on Jan. 11, 1999, the contents of each application hereby incorporated by reference in their entirety.

BACKGROUND OF THE INVENTION

The present invention broadly concerns arthrodesis for stabilizing the spine. More specifically, the invention provides open-chambered intervertebral spacers, instruments for implanting the spacers and methods for promoting fusion bone growth between adjacent vetebrae.

Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts are often used to fill the intervertebral space to prevent disc space collapse and promote fusion of the adjacent vertebrae across the disc space. In early techniques, bone material was simply disposed between the adjacent vertebrae, typically at the posterior aspect of the vertebra, and the spinal column was stabilized by way of a plate or rod spanning the affected vertebrae. Once fusion occurred, the hardware used to maintain the stability of the segment became superfluous and was a permanent foreign body. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intradiscal implant that could be used to replace a damaged disc and maintain the stability of the disc interspace between the adjacent vertebrae, at least until complete arthrodesis is achieved. The implant must provide temporary support and allow bone ingrowth. Success of the discectomy and fusion procedure requires the development of a contiguous growth of bone to create a solid mass because the implant may not withstand the compressive loads on the spine for the life of the patient.

Several metal spacers have been developed to fill the void formed and to promote fusion. Sofamor Danek Group, Inc., (1800 Pyramid Place, Memphis, Tenn. 38132, (800) 933-2635) markets a number of hollow spinal cages. For example, U.S. Pat. No. 5,015,247 to Michelson and U.S. Ser. No. 08/411,017 to Zdeblick disclose a threaded spinal cage. The cages are hollow and can be filled with osteogenic material, such as autograft or allograft, prior to insertion into the intervertebral space. Apertures defined in the cage communicate with the hollow interior to provide a path for tissue growth between the vertebral endplates. In many cases, in order to provide spacers having sufficient load bearing capacity, two spacers must be bilaterally placed in the intervertebral space. The challenge in bilateral placement is to use properly sized spacers having sufficient load bearing capacity so that they will provide adequate support and will not extend outside of the intervertebral space where they could interfere with other spinal-associated structures, including the various spinal nerves and blood vessels. A need therefore exists for such spacers. The present invention addresses this need.

SUMMARY OF THE INVENTION

This invention provides preferred interbody fusion spacers having features allowing for side-loading of substances into an interior cavity and also preferably allowing them to nest within each other, and thus allowing close placement of one or more spacers within the intervertebral space, tools for implanting the spacers and methods for promoting fusion bone growth between adjacent vertebrae. In one form of the invention, the spacers include an elongated body having a first end, a second end, an outer surface and a side wall connecting the first and second end. The elongated body defines a chamber, or interior cavity, that may optionally be filled with osteogenic material. At least one of the first and second ends, preferably both, has a discontinuity, such as a concave surface, for nesting with an adjacent spacer. The side walls of the inventive spacers define an opening to the interior cavity in a side of the elongated body, for loading a substance such as an osteogenic or osteoconductive substance, into the interior cavity.

In yet other forms of the invention, the spacers include an elongated body having a circumference, a first end wall, a second end wall, an outer surface and a side wall connecting the first and second end. The body defines a chamber, or interior cavity, and preferably has a plurality of openings for bone ingrowth that extend from the outer surface of elongated body into the interior cavity. In one embodiment, the side walls define a large opening communicating with the internal cavity of the spacer, for example extending from about 10% to about 50% around the circumference of the body, and extending along at least about 50% of the length of the body. The end walls are preferably configured for nesting with an adjacent spacer. Preferably, the discontinuities in the end walls and side walls both extend about the circumference of the body to substantially the same extent.

In other aspects of the invention, interbody fusion implant systems are provided. In one form of the invention, the systems include a first interbody fusion spacer as described above, along with a second interbody fusion spacer as defined above. The second interbody fusion spacer may or may not have discontinuities in the end and/or side walls similar to those in the first spacer.

Tools for implanting spacers are also provided. The tools include spacer engaging means for engaging a spacer and occlusion means for blocking an opening defined in the spacer. In one form of the invention, the engaging means includes a shaft slidingly disposed within a housing and having a threaded post for engaging a threaded tool hole in the spacer. In some embodiments, the occlusion means includes a plate extendible from the housing. In one specific embodiment, the plate defines a groove which is disposed around a fastener attached to the housing so that the plate is slideable relative to the housing.

Yet other aspects of the invention provide methods for promoting fusion bone growth between adjacent vertebrae. In one embodiment, a method includes providing the inventive spacers having an elongated body described above, preparing the adjacent vertebrae to receive the elongated body of the spacer in an intervertebral space between adjacent vertebrae and placing the body in the intervertebral space. In certain embodiments, two spacers can be bilaterally positioned.

The combination of the spacers of this invention with the tools and methods of this invention provide a versatile spacer without any compromise in biomechanical integrity. The spacers can be packed before or after implantation, preferably before.

Accordingly, it is one object of this invention to provide interbody fusion spacers and methods for using the spacers in an arthrodesis procedure.

Another object is to improve patient incidence of safe and satisfactory spinal stabilization and fusion.

Yet another object of the present invention is to provide spacers with good biomechanical features and osteogenic and fusion promoting features.

BRIEF DESCRIPTION OF THE DRAWINGS

FIG. 8 is a side perspective view of another embodiment of an interbody fusion implant system, showing spacers bilaterally placed with their chambers, or interior cavities, facing each other.

FIG. 9 is a top perspective view of one embodiment of an insertion tool of the present invention.

FIG. 10 is a side perspective view of the tool of FIG. 9.

FIG. 16 is a side perspective view of a tool-spacer assembly.

FIG. 17 is a top perspective view of a fastener of an insertion tool.

FIG. 18 is a top elevational view of the fastener of FIGS. 16 and 17.

FIG. 19 is a side elevational view of the fastener of FIG. 17.

DESCRIPTION OF THE PREFERRED EMBODIMENTS

Figure 1:
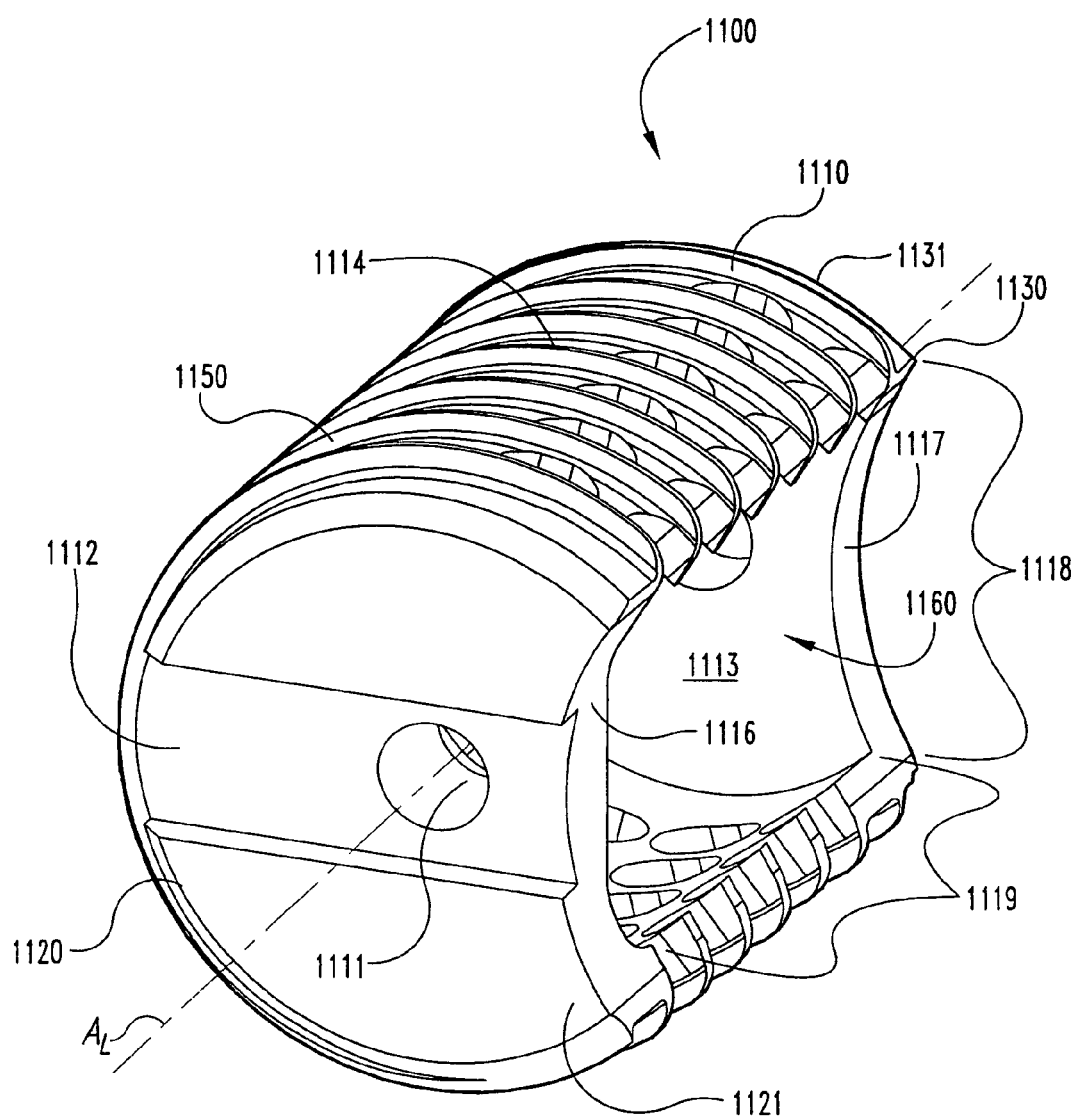
FIG. 1 is a side perspective view of one embodiment of an interbody fusion spacer of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

This invention provides interbody fusion spacers having side-openings preferably along with features allowing them to nest within each other, thus allowing close placement of one or more, typically a pair of, spacers within the intervertebral space. These spacers are advantageous for exposure of vertebral tissue to osteogenic material within the interior cavities. The design of these spacers conserves material without compromising biomechanical properties of the spacer, while allowing packing of the spacer with autologous bone chips or another suitable osteogenic or osteoconductive material through a side wall thereof. Accordingly, in one aspect of the invention, inventive interbody fusion spacers are provided that include discontinuities in side walls thereof, and preferably also that are configured for nesting with adjacent spacers. In other aspects of the invention, interbody fusion implant systems are provided that may include an interbody fusion spacer nested within another spacer, including one of the inventive interbody fusion spacers of the present invention. Other aspects of the invention include methods of promoting fusion bone growth in the space between adjacent vertebrae as well as inventive tools for placement of the spacers of the present invention.

Figure 3:
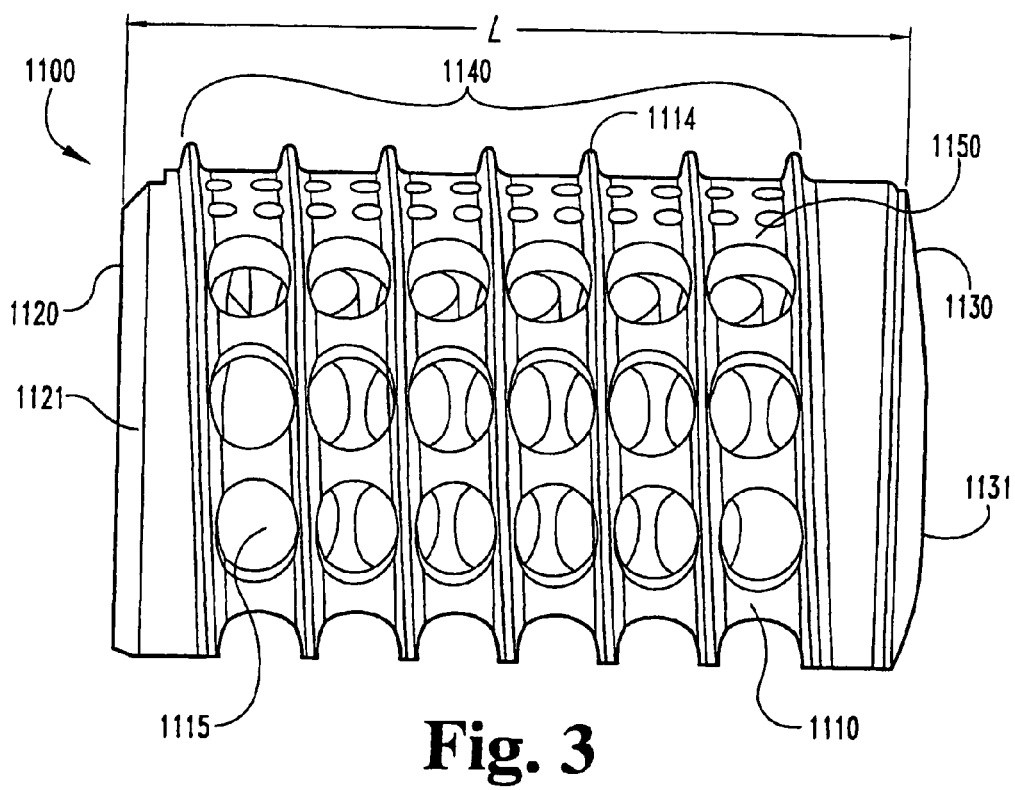
FIG. 3 is a top view of the spacer shown in FIG. 1.

Referring now to FIGS. 1 and 3, one embodiment of an interbody fusion spacer 1100 is shown. Spacer 1100 includes a body 1110 that is generally cylindrical in shape. Body 1110 includes an outer surface 1150, an end 1120 that defines end wall 1121 and an end 1130 that defines end wall 1131. Body 1110 further includes side wall 1140 that connects end 1120 and end 1130.

Body 1110 is generally hollow, defining a hollow interior cavity, or chamber, 1113. Osteogenic and/or osteoconductive material, as further described below, may advantageously be placed in interior cavity 1113. As further seen in FIG. 1, side wall 1140 defines an opening 1160, such as a side-access opening, to interior cavity 1113 in a side of body 1110. Interior cavity 1113 is in communication with opening 1160. Opening 1160 may thus provide access to interior cavity 1113 before or after implantation or can facilitate insertion of spacer 1100 into the intervertebral space. Due to the presence of the side-access opening 1160 of body 1110, its end walls can be optionally substantially closed, fixed and non-removable. For example, such end walls can be integral with the side walls. It is preferred that the wall that is inserted first into the intervertebral space, such as end wall 1131, is closed and may be positioned to protect the spinal cord from escape or leakage of any osteogenic material from interior cavity 1113 when the spacer is placed by an anterior approach.

Figure 6:
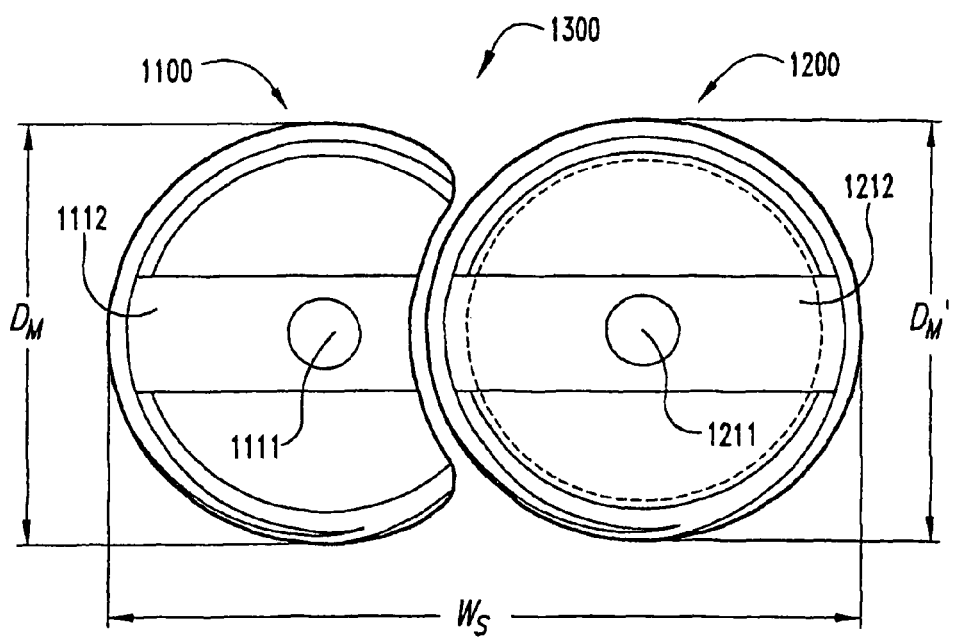
FIG. 6 is a side view of the implant system of FIG. 4.

As can further be seen in FIG. 1, at least one of the ends is advantageously configured for nesting with an adjacent spacer. In one preferred form of the invention, each of the ends has a concave discontinuity 1118. As can further be seen in FIG. 1, opening 1160 is further defined by discontinuity 1119 extending along the length of body 1110. The discontinuities advantageously expose surfaces that are configured to receive a surface of an adjacent spacer having a complimentary exterior profile. For example, the discontinuities may expose concave surfaces 1116 and 1117 of end walls 1121 and 1131, respectively. Nesting between adjacently-placed spacers may occur by having concave surfaces 1116 and 1117 receive an outer concave surface of an adjacent spacer. The ends are therefore configured such that when at least one of the spacers having a discontinuity is combined with another spacer to form an implant system, the width $W_s$ of the implant system is typically less than the sum of the combined maximum diameters $D_M$, $D_{M'}$ of the individual spacers, as best seen in FIG. 6.

In the preferred device, the discontinuity 1118 in the end walls of body 1100 will span at least about 10% of the circumference of the body 1100, more preferably at least about 20% of the circumference. Discontinuity 1118 will preferably not exceed about 50% of the circumference of the body, more preferably not exceeding about 40% of the circumference.

Thus, where the body is substantially circular in cross section as shown, end walls 1121 and 1131 and side wall 1140 will have external surfaces defining an external profile in the shape of an arc of a circle, extending no greater than about 324° C. around the circle (90% of the circumference), more preferably no greater than about 288° around the circle (80% of the circumference). Correspondingly also, the arc defined by the end walls and side walls will preferably not be less than about 180° (50% of the circumference), and more preferably not less than about 216°. In the preferred devices, the remaining external profile of the end walls define a concave surface, configured for nesting with an adjacent spacer.

Discontinuity 1119 along the length of the body, which preferably extends substantially parallel to the longitudinal axis of body 1110, will preferably span at least about 50% of the length of the body, more preferably at least about 80%, and will most preferably span substantially the entire length of the side wall 1140. Moreover, the circumferences of the side wall and end walls desirably extend uniformly along the length of the body. Furthermore, in a preferred device, the side wall and end walls extend about the circumference of body 1110 to substantially the same extent.

Body 1110 further preferably includes a plurality of smaller openings 1115 for bone ingrowth. Openings 1115 preferably extend from outer surface 1150 of body 1110 into interior cavity 1113.

The spacers of the invention are typically sized, or configured, to fit within an intervertebral space. One skilled in the art is aware that the size will depend on the specific circumstances, including the size of the recipient and the location in the spine into which the spacers will be positioned.

The spacers of the invention may be provided with surface features defined in outer surface 1150. A wide variety of surface features are contemplated. In one form of the invention, end 1120 is a tool engagement end that defines a tool engaging or instrument attachment hole 1111 as seen in FIG. 1. In a preferred embodiment, hole 1111 is threaded but any suitable configuration is contemplated.

Figure 2:
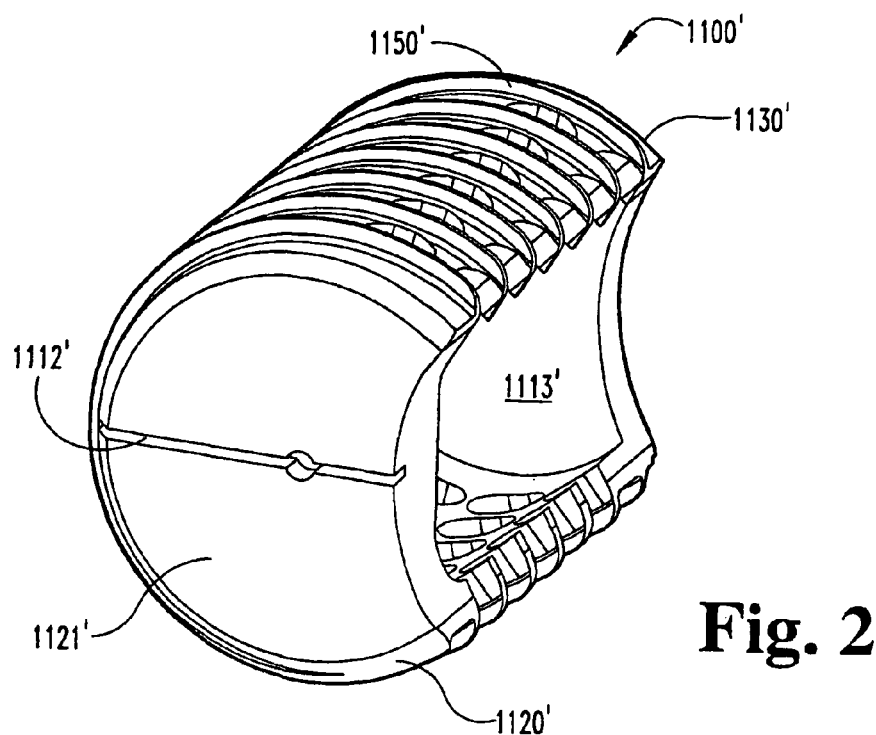
FIG. 2 is a side perspective view of another embodiment of an interbody fusion spacer.

Spacers of the present invention may further include a tool-engaging slot 1112 for receiving an implantation tool. The slot is typically perpendicular to the central longitudinal axis $A_L$ of spacer 1100. In yet other embodiments, slot 1112 may form an alignment score mark or groove 1112' defined in tool engagement end 1120' of spacer 1100' as seen in FIG. 2, thus making the opposite end, where end wall 1130' is located, the insertion end. Spacer 1100' is identical in all respects to spacer 1100, except for the difference in the feature present on the end walls. Thus, components of spacer 1100' are numbered correspondingly to those of spacer 1100, except with a denoting prime (') symbol. Alternatively, a projection may be formed on the end walls instead of a slot. Such a projection may form a straight, flat-sided shape (such as a mirror image of the slot depicted in FIG. 1), an elliptical eminence, a bi-concave eminence, a square eminence, or any other protruding shape which provides sufficient end-cap or tool engaging end strength and drive purchase to allow transmission of insertional torque without breaking or otherwise damaging the eminence.

Yet other surface features can be defined along the length L of the spacer. Referring again to FIGS. 1 and 3, outer surface of spacer 1100 may defines threads 1114 as illustrated, and/or other expulsion-resisting proturbances. The threads may be made by methods and tools well known in the art. The threads provide many advantages. For example, the thread feature increases postoperative stability of the spacer by engaging the adjacent vertebral endplates and anchoring the spacer to prevent expulsion. The threads also stabilize the bone-spacer interface and reduce micromotion to facilitate fusion.

Interior cavity 1113 may be packed with any suitable osteogenic or osteoconductive material. In a preferred embodiment, the material M is sized so that it will contact the endplates of the adjacent vertebrae when the spacer is implanted within the vertebrae. This provides better contact of the composition with the endplates to stimulate bone ingrowth. Osteogenic material may advantageously be disposed in interior cavity 1113 through side-access opening 1160. Thus, opening 1160 is preferably sized to allow passage of osteogenic material into the interior cavity, or chamber 1113.

Any suitable osteogenic or osteoconductive material or composition is contemplated, including autograft, allograft, xenograft, demineralized bone, synthetic and natural bone graft substitutes, such as bioceramics, polymers, and osteoinductive factors. The terms osteogenic material or osteogenic composition as used herein mean virtually any material that promotes bone growth or healing including autograft, allograft, xenograft, bone graft substitutes and natural, synthetic and recombinant proteins, hormones and the like.

Autograft can be harvested from locations such as the iliac crest using drills, gouges, curettes, trephines and other tools and methods which are well known to surgeons in this field. Preferably, autograft is harvested from the iliac crest with a minimally invasive donor surgery. The osteogenic material may also include bone reamed away by the surgeon while preparing the end plates for the spacer.

Advantageously, where autograft is chosen as the osteogenic material, only a very small amount of bone material is needed to pack the chamber. The autograft itself is not required to provide structural support as this is provided by the spacer. The donor surgery for such a small amount of bone is less invasive and better tolerated by the patient. There is usually little need for muscle dissection in obtaining such small amounts of bone. The present invention therefore eliminates or minimizes many of the disadvantages of employing autograft.

Natural and synthetic graft substitutes which replace the structure or function of bone are also contemplated for the osteogenic composition. Any such graft substitute is contemplated, including for example, demineralized bone matrix, mineral compositions and bioceramics. As is evident from a review of *An Introduction to Bioceramics*, edited by Larry L. Hench and June Wilson (World Scientific Publishing Co. Ptd. Ltd, 1993, volume 1), there is a vast array of bioceramic materials, including BIOGLASS®, hydroxyapatite and calcium phosphate compositions known in the art which can be used to advantage for this purpose. That disclosure is herein incorporated by reference for this purpose. Preferred compositions include bioactive glasses, tricalcium phosphates and hydroxyapatites. In one embodiment, the graft substitute is a biphasic calcium phosphate ceramic including tricalcium phosphate and hydroxyapatite.

In some embodiments, the osteogenic compositions used in this invention may comprise a therapeutically effective amount to stimulate or induce bone growth of a substantially pure bone inductive or growth factor or protein in a pharmaceutically acceptable carrier. The preferred osteoinductive factors are the recombinant human bone morphogenetic proteins (rhBMPs) because they are available in unlimited supply and do not transmit infectious diseases. Most preferably, the bone morphogenetic protein is a rhBMP-2, rhBMP-4 or heterodimers thereof.

Recombinant BMP-2 can be used at a concentration of about 0.4 mg/ml to about 1.5 mg/ml, preferably near 1.5 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

The choice of carrier material for the osteogenic composition is based on biocompatibility, biodegradability, mechanical properties and interface properties as well as the structure of the load bearing member. The particular application of the compositions of the invention will define the appropriate formulation. Potential carriers include calcium sulphates, polylactic acids, polyanhydrides, collagen, calcium phosphates, polymeric acrylic esters and demineralized bone. The carrier may be any suitable carrier capable of delivering the proteins. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is a biphasic calcium phosphate ceramic. Ceramic blocks are commercially available from Sofamor Danek Group, B. P. 4-62180 Rang-du-Fliers, France and Bioland, 132 Rou d Espangne, 31100 Toulouse, France. The osteoinductive factor is introduced into the carrier in any suitable manner. For example, the carrier may be soaked in a solution containing the factor.

Figure 4:
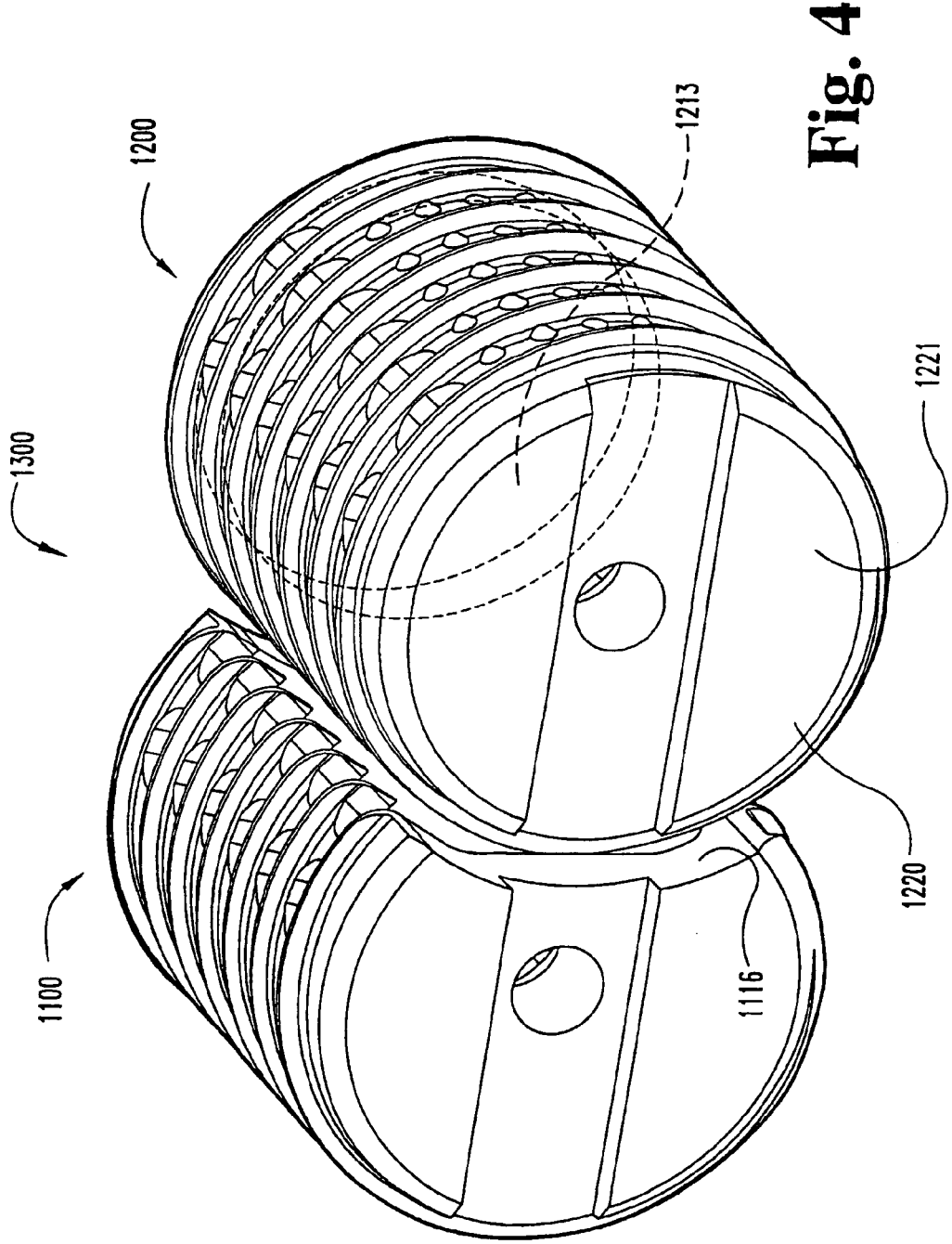
FIG. 4 is a side perspective view of one embodiment of an interbody fusion implant system of the present invention.
Figure 5:
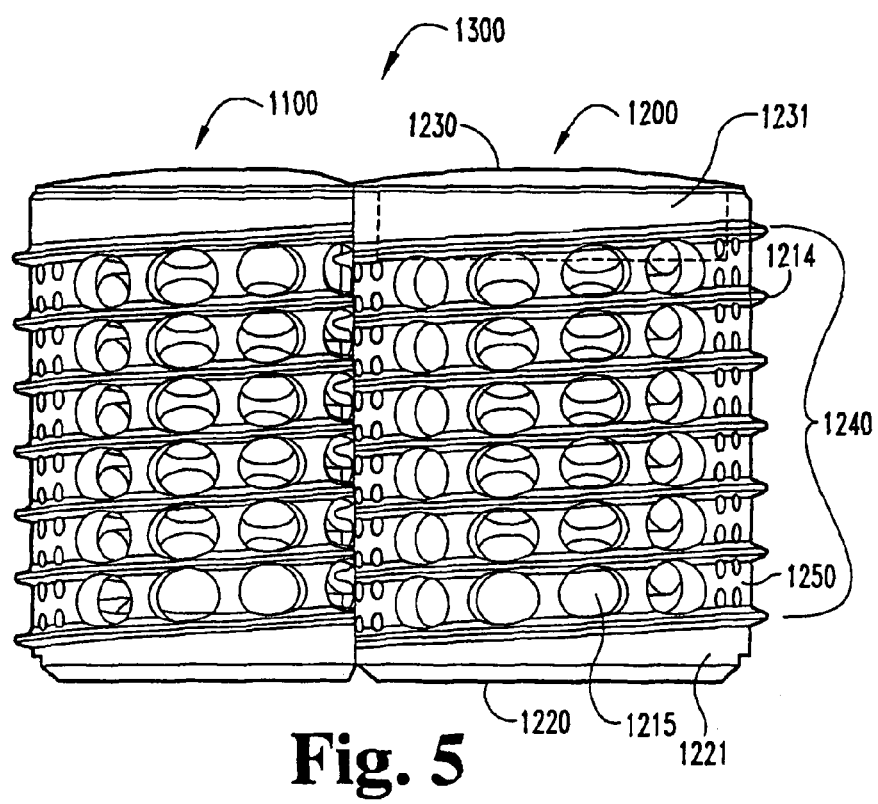
FIG. 5 is a top view of the implant system of FIG. 4.
Figure 7:
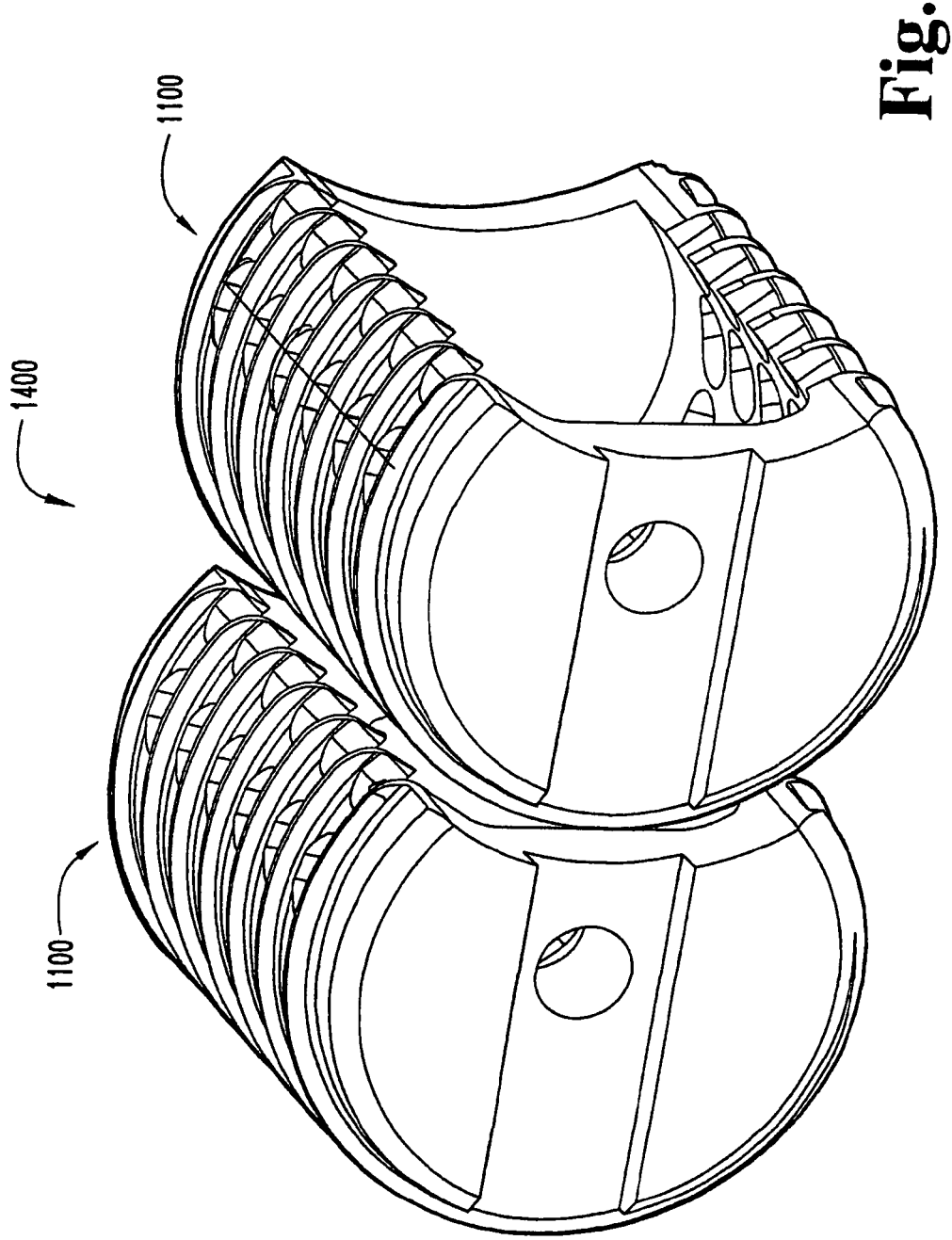
FIG. 7 is a side perspective view of another embodiment of an interbody fusion implant system of the present invention.

In another aspect of the invention, an interbody fusion implant system is provided. The system includes one of the inventive spacers described above, along with either another of the inventive spacers, or with other spacers known to the art. Referring now to FIGS. 4-6, implant system 1300 may include spacer 1100 combined with an adjacent spacer 1200 to provide a nested implant system. Spacer 1200 is of a design similar to that of spacer 1100 having all the features thereof, except it does not have the wall discontinuities. Thus, spacer 1200 preferably has either a removable or non-removable end wall, or cap, 1221, more preferably in the tool engaging end 1220. Moreover, spacer 1200 may include, for example, instrument attachment hole 1211, tool engaging slot 1212, side wall 1240, outer surface 1250, openings 1215 for bone ingrowth, end walls 1221 and 1231, internal cavity 1213 and threads 1214. It is also seen that the width $W_s$ of system 1300 is less than the sum of the maximum diameter $D_M$ of spacer 1100 and the maximum diameter $D_{M'}$ of spacer 1200. Such is the preferred configuration present in the implant systems described herein. In yet other forms of the invention as depicted in FIG. 7, two spacers 1100 can be placed adjacent to one another to provide implant system 1400.

In yet another embodiment, two spacers 1100 can optionally be aligned such that the side-wall openings 1160 face one another as seen in FIG. 8, thus forming implant system 1400'. The spacers are of the invention can be formed of any suitable biocompatible material, including metals, ceramics, polymers, composites, and alloys. A preferred material includes metals, including metal alloys. Some embodiments include titanium, stainless steel, and Hedrocel®.

The spacers described herein may be conveniently implanted with known instruments and tools. Any instrument which will firmly hold the implant and permit the implant to be inserted is contemplated. Preferably, the instrument will be adapted to compensate for the open structure of the inventive spacers described herein.

Accordingly, yet another aspect of the invention provides insertion devices for facilitating the implantation of spacers, implants and osteogenic material. The tools include spacer engaging means for engaging a spacer or other item and occlusion means for blocking an opening defined in the spacer.

Referring now to FIGS. 9-12, one embodiment of an insertion tool 800' is provided which includes a housing 805' having a proximal end 806' and an opposite distal end 807' and defining a passageway 810' between the two ends. A shaft 815' which has a first end 816' and an opposite second end 817' is disposed within the passageway 810'. The first end 816' of the shaft 815' is adjacent the distal end 807' of the housing 805'. The first end 816 defines a spacer engager 819'. An occlusion member 820' is attached to the housing 805'.

Figure 11:
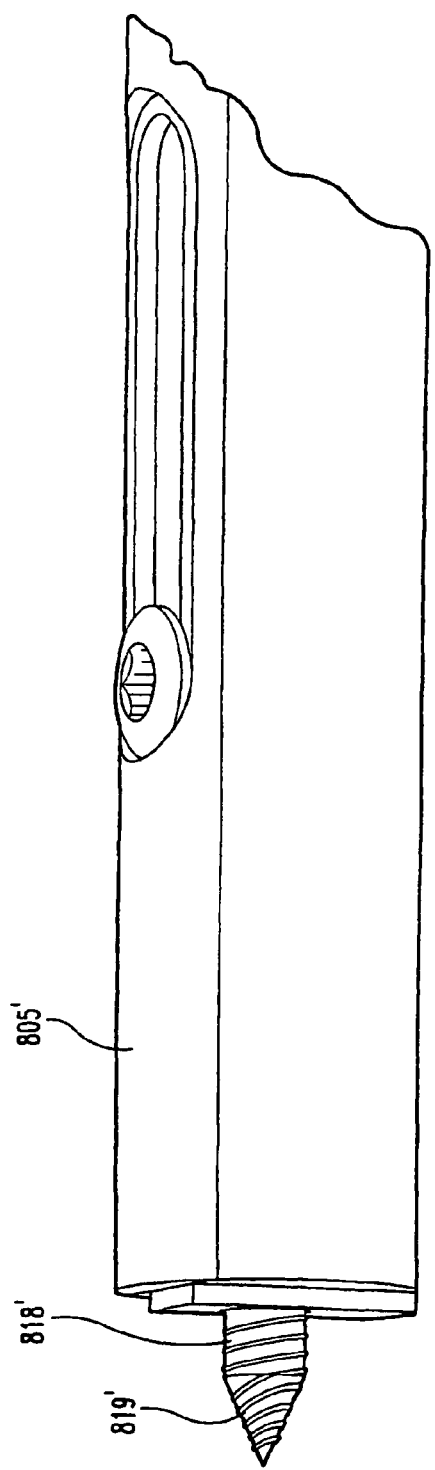
FIG. 11 is a perspective view of a spacer engaging element of an insertion tool.
Figure 12:
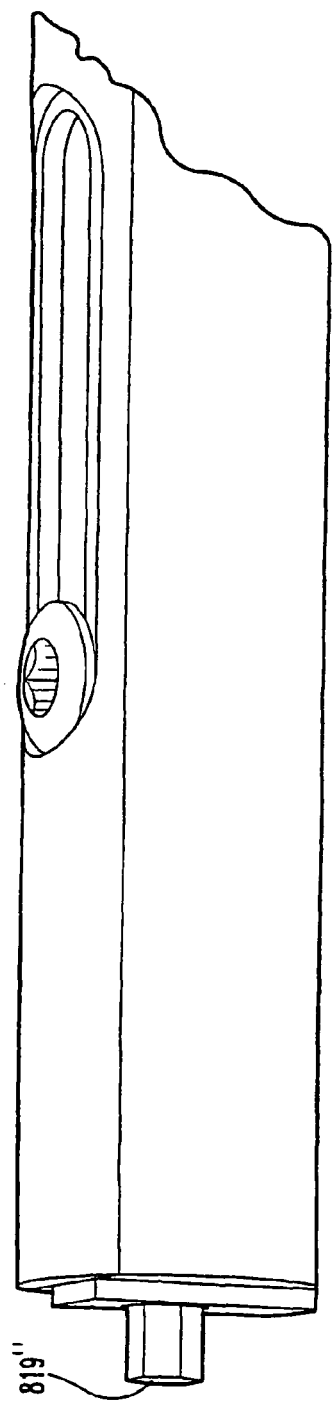
FIG. 12 is a perspective view of a spacer engaging element of an insertion tool.

The spacer engager 819' has any configuration which will engage a spacer. In some embodiments the spacer engager 819' includes a post 818' as shown in FIG. 11 for engaging a hole in the spacer. The post 818' may have any configuration which will provide for mating engagement with a hole in a spacer. For example, in preferred embodiments, the engager 819' is threaded as shown in FIG. 11 to matingly engage a threaded tool hole. Other embodiments include sharply pointed tip 819' as shown in FIG. 9 or a hexagonal shaped tip 819" as shown in FIG. 12. In each case, the engager is shaped and sized to mate engagingly with the tool hole of the spacer. In other embodiments, the spacer engaging means is a pair of prongs having opposite facing spacer engaging members for grasping an outer surface of the spacer.

Figure 13:
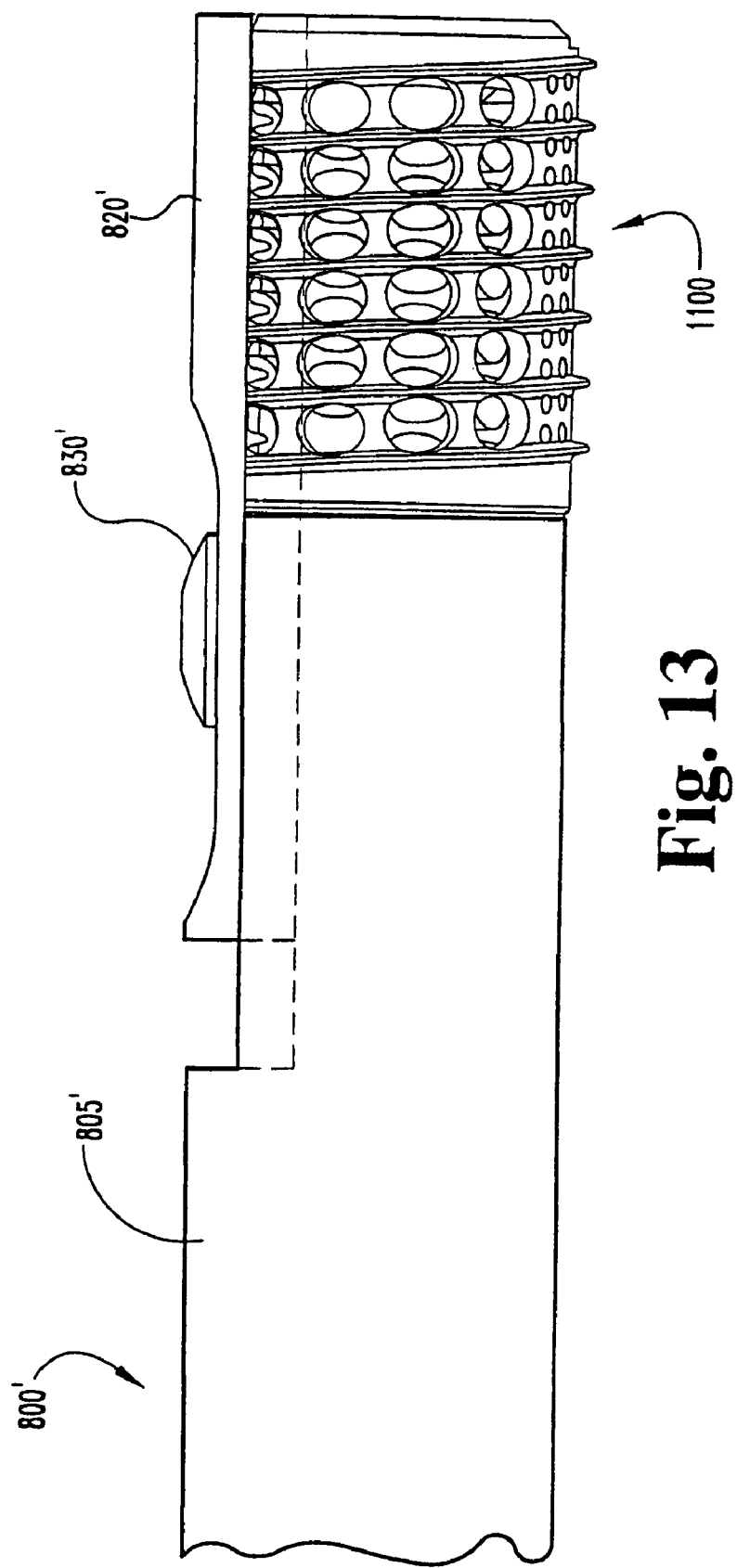
FIG. 13 is a side elevational view of an insertion tool engaged to a spacer.

The spacer insertion tool 800' also includes an occlusion member 820' for blocking an opening defined in the spacer when the spacer engager 819' is engaged to the spacer. In a preferred embodiment, the occlusion member 820' is extendible from the distal end 807' of the housing 805' for blocking an opening in the spacer. As shown in FIG. 13, the occlusion member 820' closes the opening 1160 to interior cavity 1113 of spacer 1100.

Figure 14:
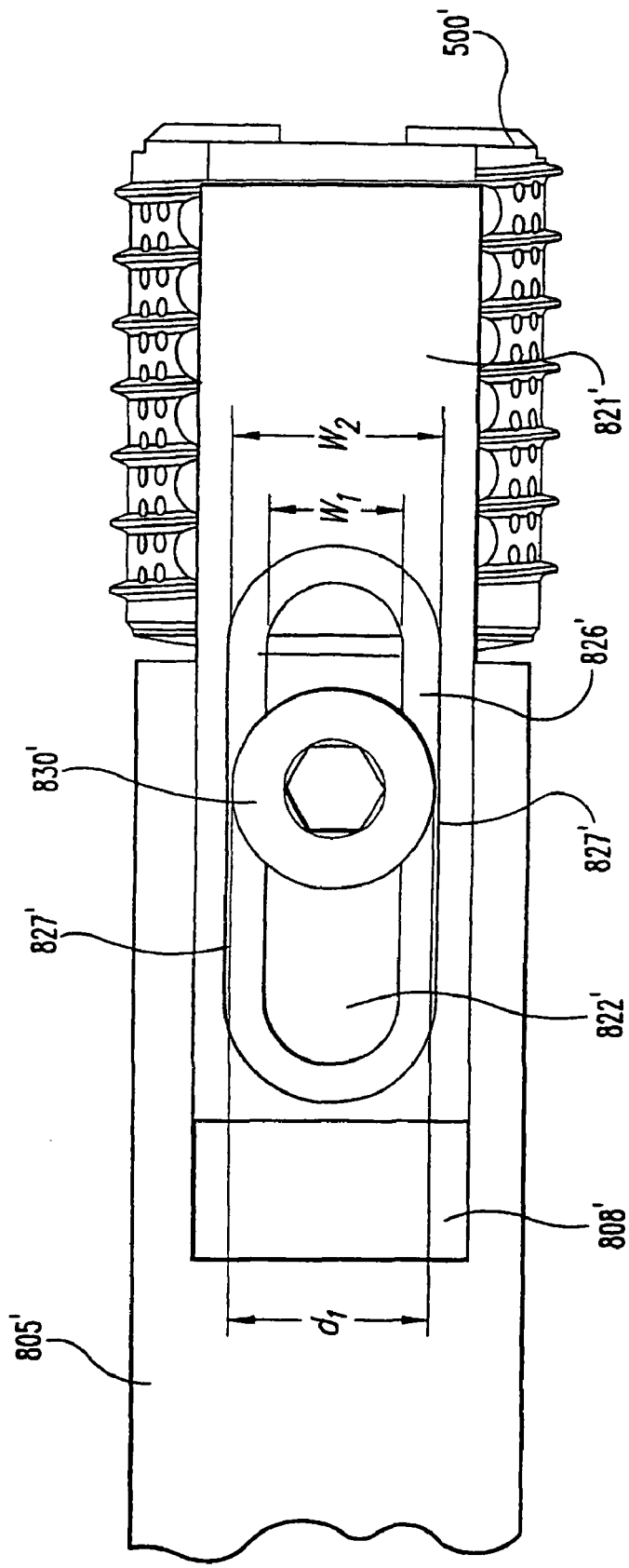
FIG. 14 is a top perspective view of the view shown in FIG. 13.

The occlusion member 820' is preferably slideably engaged to the housing 805'. Referring now to FIG. 14, in one embodiment, the occlusion member 820' includes a plate 821' which defines a groove 822'. A fastener 830' is engaged to a fastener bore 809' (seen in FIG. 10) in the housing 805' and the groove 822' is disposed around the fastener 830'. In this way, the plate 821' is slideable relative to the housing 805'.

Figure 15:
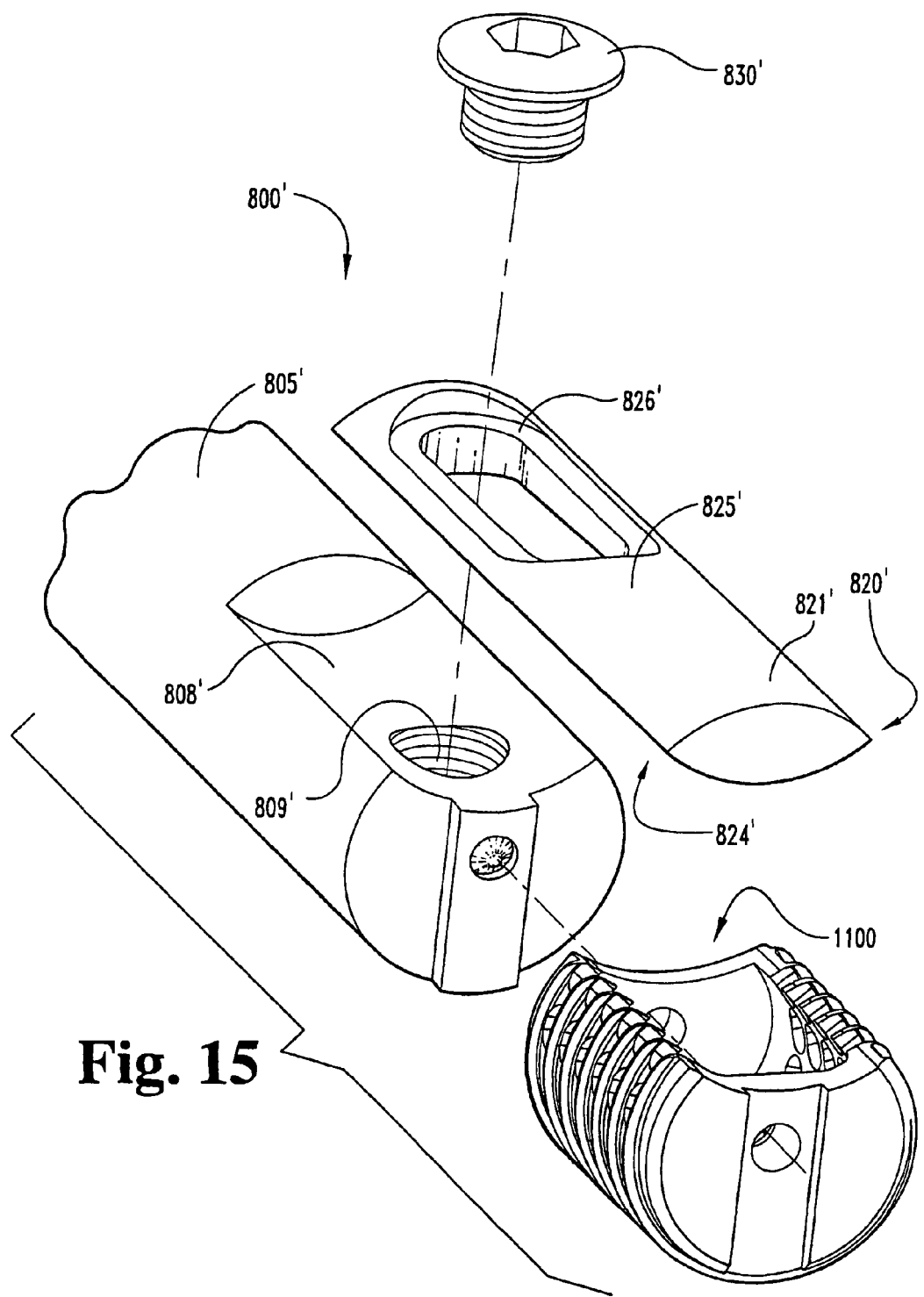
FIG. 15 is an exploded side perspective view of a tool-spacer assembly of the present invention.

As shown in FIG. 15, the housing 805' is preferably provided with a recess 808' which is defined to accept the occlusion member 820' without increasing the effective diameter of the device 800'. The occlusion member is also adapted for the best fit with the spacer. For example, the interior surface 824' of the occlusion member is preferably curved to complement the concave-shaped discontinuity of the inventive spacers described herein. Referring now to FIGS. 15 and 16, the plate 821' of the occlusion member 820' preferably includes a curved superior surface 825' which approximates and completes the minor diameter of spacer 1100 when the spacer engager 819' is engaged to the tool engaging hole 1111 and the occlusion member 820' is blocking opening 1160 of spacer 1100. Preferably, the plate 821' and the end walls 1121 and 1131 of spacer 1100 will be configured such that curved superior surface 825' will not increase the maximum diameter $D_M$ of the threaded outer surface 1150 when the tool is engaged to the spacer. This facilitates rotation and screw insertion of the spacer and occlusion member combination into an intervertebral space. The occlusion member 820' preferably has an interior surface 824' which is convexly curved to complement the concave surfaces of end walls 1121 and 1131 of spacer 1100. Correspondingly, recess 808' of insertion tool 800' has a concave surface complementary to convexly curved surface 824' of occlusion member 820'. Further, occlusion member 820' is of a length and design sufficient to span to the distal end of the engaged spacer 1100, as depicted in FIG. 13. Occlusion member 820' can also have a beveled outer end as depicted, or an otherwise smoothed outer end, to facilitate rotary insertion.

The tool 800' depicted in FIG. 9 also includes a handle portion 840'. The handle portion includes means for slidingly moving the shaft 815' within the housing 805' and for rotating the post 818'. In the embodiment shown in FIGS. 9 and 10 the means includes a thumbwheel 841'. In some embodiments, the handle portion 840' has a Hudson end attachment 842'.

Referring now to FIGS. 17-19, the fastener 830' is preferably provided with a housing engaging means shown in FIG. 17 as a post 834', and a plate engaging means or head portion 835'. The fastener 830' preferably includes an internal hex 837' for receiving a fastener driving tool. The post portion 834' may be threaded for mating engagement with threaded bore 809' in the housing 805'. In preferred embodiments shown in FIGS. 14 and 16, the plate 821' defines a recess 826 surrounding the groove 822'. The diameter $d_1$ of the head portion 835 is greater than the diameter $d_2$ of the post 834'. The diameter $d_2$ is less than the width $w_2$ of the groove 822'. The diameter $d_1$ of the head portion is greater than width $w_1$ but preferably no greater than the distance $w_2$ between the outer edges 827' of the recess 826'. Thus, the head portion 835' of the fastener 830 can rest on the recess 826 while the post portion 834' extends through the groove 822'. In this way, plate 821' is slidable relative to the housing 805'. This also provides for a low profile device which can be inserted into various cannula for percutaneous procedures.

The spacers and tools in this invention can be conveniently incorporated into known surgical, preferably minimally invasive, procedures. The spacers of this invention can be inserted using laparoscopic technology as described in Sofamor Danek USA's *Laparoscopic Bone Dowel Surgical Technique,* 1995, 1800 Pyramid Place, Memphis, Tenn. 38132, 1-800-933-2635, preferably in combination with the insertion tool 800' of this invention.

The combination of spacers of this invention with the tools of this invention allow the spacers to provide the benefits of a nestable spacer without suffering any biomechanical disadvantage. The occlusion member 825' blocks the side-opening of the spacer to lessen the stress on the wall of the spacer for smooth insertion. The occlusion member also allows the chamber, or interior cavity, to be packed with osteogenic material before the spacers are implanted. In some procedures, two open spacers are packed with their side-openings facing one another as depicted in FIG. 8. The side-opening of the spacers, along with the tools described herein, allow the spacers to be packed closely together because virtually no clearance is required for the insertion tool. The side-opening also allows the interior cavity to be packed after the spacer is implanted.

Figure 20:
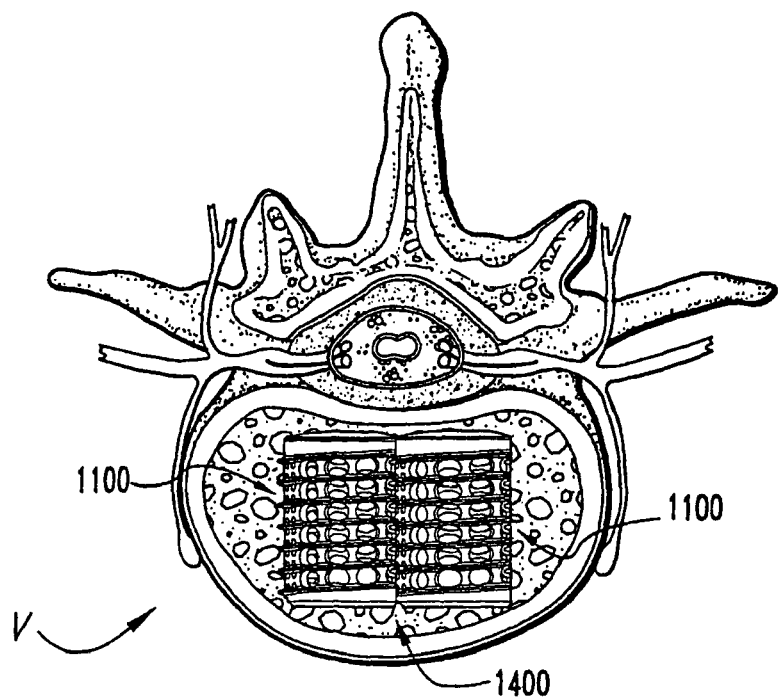
FIG. 20 is a top elevational view of an implant system of the present invention implanted within an intervertebral space via an anterior surgical approach.

In other aspects of the invention, methods of promoting fusion bone growth in the space between adjacent vertebrae are provided. In one form of the invention, the method includes providing a first interbody fusion spacer described herein, such as one in which each end has a surface for nesting with an adjacent spacer and having a first side wall defining an opening to the interior cavity in a side of the spacer body. The spacer selected is of the appropriate dimensions, based on the size of the cavity created and the needs of the particular patient undergoing the fusion. The adjacent vertebrae are prepared to receive the spacer in an intervertebral space between adjacent vertebrae according to conventional procedures. The spacer is mounted on an instrument, preferably via an instrument attachment hole. An osteogenic material may optionally be placed within the cavity of the spacer and the opening of the spacer is then blocked with an occlusion member of the instrument. The spacer is then inserted into the cavity created between the adjacent vertebrae to be fused. Once the spacer is properly oriented within the intervertebral space, the occlusion member of the instrument can be withdrawn form the spacer aperture and the spacer engager is disengaged from the spacer. In a preferred form of the invention, a second spacer is inserted into the intervertebral space after the first spacer is properly positioned near vertebral body V, resulting in bilateral placement of the spacers as seen in FIG. 20. The second spacer may be the same as the first spacer, as seen in FIG. 20 with two spacers 1100 that form implant system 1400, or may be any other spacer described herein or other appropriate spacer known in the art. To this end, implant systems 1300, 1400, or 1500, for example, may be advantageously used in the present invention. Osteogenic material may also optionally be placed within those spacers having chambers therein.

Figure 21:
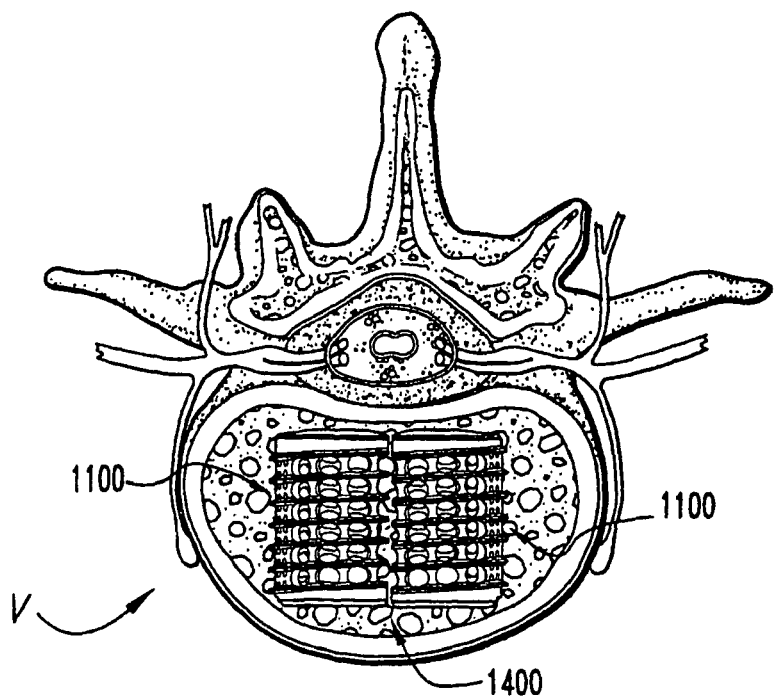
FIG. 21 is a top elevational view of another implant system described herein implanted within an intervertebral space via an anterior surgical approach.

Bilateral placement has many advantages. For example, bilateral placement results in improved spinal support with two spacers that fit properly within the disc space. Moreover, such positioning allows for a substantial area for placement of osteogenic material which will facilitate boney bridging across the disc space, especially when the spacers are positioned with their side wall openings facing each other as seen in FIG. 21 with spacers 1100 that form implant system 1400'.

It should be understood that the embodiments described herein are for illustrative purposes only and that various modifications or changes in light thereof will be suggested to persons skilled in the art and are to be included within the spirit and purview of this application and the scope of the appended claims.

What is claimed is:

1. An interbody fusion spacer, comprising:
an elongated body having a first end wall, an opposite second end wall, and a side wall extending between said first and second end walls, said elongated body defining an outer surface and an interior chamber for receiving an osteogenic material, said side wall defining a main side wall opening in communication with said interior chamber, said main side wall opening sized and configured for loading said osteogenic material into said interior chamber, said side wall defining a plurality of secondary side wall openings extending from said outer surface and in communication with said interior chamber for bone ingrowth into said interior chamber;
wherein said elongated body comprises a generally cylindrical body having a length extending from said first end wall to said second end wall and wherein said generally cylindrical body is externally threaded along said length;
wherein said outer surface of said generally cylindrical body comprises an outer circumferential surface defining an outer circumference, said outer circumferential surface defining an external outer surface profile in the shape of an arc of a circle extending no less than 180 degrees about said outer circumference and extending along said length of said body from said first end wall to said second end wall; and
wherein said main side wall opening extends over at least about 20% of the outer circumference of said body and extends along at least about 50% of said length of said body to provide said main side wall opening with a size sufficient for loading said osteogenic material into said interior chamber.

2. The interbody fusion spacer of claim 1, wherein said main side wall opening extends along at least about 80% of the overall length of said body.

3. The interbody fusion spacer of claim 2, wherein said main side wall opening extends substantially entirely along the overall length of said body.

4. The interbody fusion spacer of claim 1, wherein said main side wall opening extends along at least about 40% of the outer circumference of said body.

5. The interbody fusion spacer of claim 1, wherein said plurality of secondary bone ingrowth openings are sized smaller than said main side wall opening.

6. The interbody fusion spacer of claim 1, wherein at least one of said first and second end walls defines a tool engaging hole for receiving a driving tool for implanting the interbody fusion spacer into an intervertebral space.

7. The interbody fusion spacer of claim 1, wherein said side wall defines a side wall discontinuity, said main side wall opening defined in said side wall discontinuity.

8. The interbody fusion spacer of claim 1, wherein each of said first and second end walls includes an end wall discontinuity defining a concave surface sized and configured for nesting with an adjacent interbody fusion spacer.

9. The interbody fusion spacer of claim 1, wherein said side wall of said elongated body defines a discontinuity circumferentially interrupting said outer circumferential surface, said discontinuity defining said main side wall opening.

10. The interbody fusion spacer of claim 9, wherein said discontinuity extends across said first and second end walls.

11. The interbody fusion spacer of claim 10, wherein said discontinuity has a concave configuration.

12. The interbody fusion spacer of claim 9, wherein said plurality of secondary bone ingrowth openings are sized smaller than said main side wall opening.

13. The interbody fusion spacer of claim 1, wherein said external outer surface profile of said outer circumferential surface extends no less than 216 degrees about said outer circumference.

14. An interbody fusion spacer, comprising:
a generally cylindrical elongated body having opposite first and second end walls and a side wall having a length extending from said first end wall to said second end wall and wherein said generally cylindrical elongated body is externally threaded along said length, said first and second end walls integral with said side wall to provide said elongated body as a unitary, single-piece structure, said elongated body defining an outer surface and an interior chamber for receiving an osteogenic material, said side wall defining a main side wall opening in communication with said interior chamber, said side wall defining a plurality of secondary side wall openings sized smaller than said main side wall opening and extending from said outer surface and in communication with said interior chamber to provide for bone ingrowth into said interior chamber; and
wherein said outer surface of said generally cylindrical elongated body comprises an outer circumferential surface defining an outer circumference, said outer circumferential surface defining an external outer surface profile in the shape of an arc of a circle extending no less than 180 degrees about said outer circumference and extending along said length of said body from said first end wall to said second end wall; and
wherein said main side wall opening is sized to extend over at least about 20% of said outer circumference of said body and along at least about 50% of said length of said elongated body to provide said side wall opening with a size sufficient for loading said osteogenic material into said interior chamber.

15. The interbody fusion spacer of claim 14, wherein said main side wall opening extends substantially entirely along the overall length of said elongated body.

16. The interbody fusion spacer of claim 14, wherein said main side wall opening extends along at least about 40% of the outer circumference of said elongated body.

17. The interbody fusion spacer of claim 14, wherein said side wall of said elongated body defines a discontinuity circumferentially interrupting said outer circumference, said discontinuity defining said main side wall opening.

18. The interbody fusion spacer of claim 17, wherein said discontinuity extends across said first and second end walls; and
wherein said discontinuity has a concave configuration.

19. The interbody fusion spacer of claim 14, wherein said external outer surface profile of said outer circumferential surface extends no less than 216 degrees about said outer circumference.

20. An interbody fusion implant system, comprising:
a first interbody fusion spacer including an elongated body having a first end wall, an opposite second end wall, and a side wall extending between said first and second end walls, said elongated body defining an outer surface and an interior chamber for receiving an osteogenic material, said side wall defining a main side wall opening in communication with said interior chamber, said main side wall opening sized and configured for loading said osteogenic material into said interior chamber, said side wall defining a plurality of secondary side wall openings extending from said outer surface and in communication with said interior chamber for bone ingrowth into said interior chamber;

wherein said elongated body comprises a generally cylindrical body;

wherein said outer surface of said generally cylindrical body comprises an outer circumferential surface defining an outer circumference; and wherein said main side wall opening extends over at least about 20% of the outer circumference of said body and extends along at least about 50% of an overall length of said body to provide said main side wall opening with a size sufficient for loading said osteogenic material into said interior chamber; and a second interbody fusion spacer having a second elongated body, said second elongated body having a third end wall, a fourth end wall, a second side wall extending between said third and fourth end walls, said second interbody fusion spacer nested within a concave discontinuity in said first interbody fusion spacer.

21. The interbody fusion implant system of claim 20, wherein said second elongated body of said second interbody fusion spacer is generally cylindrical in shape and has an outer circumferential surface defining an outer circumference; and wherein said second elongated body includes a main side wall opening in communication with an interior chamber, said main side wall opening in said second elongated body is sized to extend over at least about 20% of the outer circumference of said second elongated body and along at least about 50% of an overall length of said second elongated body to provide said main side wall opening in said second elongated body with a size sufficient for loading said osteogenic material into said interior chamber of said second elongated body.

22. The interbody fusion implant system of claim 21, wherein said main side wall opening in said second elongated body is sized to extend substantially entirely along the overall length of said second elongated body.

23. The interbody fusion implant system of claim 21, wherein said main side wall opening in said second elongated body is sized to extend along at least about 40% of the outer circumference of said second elongated body.

24. The interbody fusion implant system of claim 20, wherein said first and second end walls are non-removably fixed to said side wall; and wherein said third and fourth end walls are non-removably fixed to said second side wall.

25. The interbody fusion implant system of claim 20, wherein said first and second end walls are integral with said side wall to provide said elongated body as a first unitary, single-piece structure; and wherein said third and fourth end walls integral with said second side wall to provide said second elongated body as a second unitary, single-piece structure.

* * * * *